US008483909B2

(12) United States Patent
Visconti et al.

(10) Patent No.: US 8,483,909 B2
(45) Date of Patent: Jul. 9, 2013

(54) VEHICLE CONTROL METHOD FOR ADAPTING DYNAMIC VEHICLE PERFORMANCE TO THE PSYCHOPHYSICAL CONDITION OF THE DRIVER

(75) Inventors: Amedeo Visconti, Turin (IT); Antonio Calvosa, Milan (IT)

(73) Assignee: Ferrari S.p.A., Modena (IT)

( * ) Notice: Subject to any disclaimer, the term of this patent is extended or adjusted under 35 U.S.C. 154(b) by 421 days.

(21) Appl. No.: 12/866,716

(22) PCT Filed: Feb. 9, 2009

(86) PCT No.: PCT/IT2009/000048
§ 371 (c)(1),
(2), (4) Date: Nov. 12, 2010

(87) PCT Pub. No.: WO2009/098731
PCT Pub. Date: Aug. 13, 2009

(65) Prior Publication Data
US 2011/0213511 A1    Sep. 1, 2011

(30) Foreign Application Priority Data
Feb. 7, 2008 (IT) .............................. BO2008A0081

(51) Int. Cl.
*G06F 7/00* (2006.01)
(52) U.S. Cl.
USPC .............................. 701/36; 340/576; 180/272
(58) Field of Classification Search
USPC ................ 701/1, 36, 301, 538; 180/271, 272; 340/573.1, 575, 576
See application file for complete search history.

(56) References Cited

U.S. PATENT DOCUMENTS

| 5,172,785 | A | 12/1992 | Takahashi | |
|---|---|---|---|---|
| 6,392,550 | B1 | 5/2002 | Najor | |
| 6,906,619 | B2 * | 6/2005 | Williams et al. | 340/425.5 |
| 7,609,150 | B2 * | 10/2009 | Wheatley et al. | 340/436 |
| 7,609,168 | B2 * | 10/2009 | Boverie | 340/576 |

(Continued)

FOREIGN PATENT DOCUMENTS

| DE | 4407935 A1 | 9/1994 |
|---|---|---|
| WO | 2007090896 A1 | 8/2007 |

OTHER PUBLICATIONS

International Search Report PCT/IT2009/000048 dated Jun. 24, 2009.

(Continued)

*Primary Examiner* — Richard M. Camby
(74) *Attorney, Agent, or Firm* — McCracken & Frank LLC

(57) ABSTRACT

A method of controlling a driver-operated vehicle; the method including the steps of:
recording the values of a number of psychophysical parameters of the driver over a first measuring interval; making a first evaluation of the driver's psychophysical condition on the basis of the driver's psychophysical parameter values over the first measuring interval; recording the values of the driver's psychophysical parameters over a second measuring interval following the first measuring interval; making a second evaluation of the driver's psychophysical condition on the basis of the driver's psychophysical parameter values over the second measuring interval; comparing the first and second evaluation of the driver's psychophysical condition to determine a change in the driver's psychophysical condition; and modifying the dynamic performance of the vehicle as a function of the driver's psychophysical condition, to adapt dynamic performance of the vehicle to the change in the driver's psychophysical condition.

7 Claims, 2 Drawing Sheets

U.S. PATENT DOCUMENTS

| | | | |
|---|---|---|---|
| 8,339,268 B2 * | 12/2012 | Deng et al. | 340/575 |
| 2003/0153846 A1 | 8/2003 | Marple-Horvat | |
| 2005/0030184 A1 | 2/2005 | Victor | |
| 2005/0148894 A1 * | 7/2005 | Misczynski et al. | 600/513 |
| 2006/0235753 A1 | 10/2006 | Kameyama | |

OTHER PUBLICATIONS

International Preliminary Report on Patentability PCT/IT2009/000048 dated Apr. 30, 2010.

* cited by examiner

VEHICLE CONTROL METHOD FOR ADAPTING DYNAMIC VEHICLE PERFORMANCE TO THE PSYCHOPHYSICAL CONDITION OF THE DRIVER

TECHNICAL FIELD

The present invention relates to a vehicle control method.

The present invention may be used to advantage in a passenger car, to which the following description refers purely by way of example.

BACKGROUND ART

To make driving safer, modern cars are equipped with various electronic driving-aid devices, such as an ABS (Anti Block System—to prevent the wheels blocking when braking), ESP (Electronic Stability Program—to control vehicle stability), ASP (Anti Skid Program—to prevent the drive wheels from skidding), and an electronic suspension control system (to adjust mechanical response of the suspensions to external stress).

Some cars are also equipped with a selection device which allows the driver to select and communicate a given dynamic vehicle performance to a central control unit, which accordingly adjusts the operating parameters of the electronic driving-aid devices to match dynamic vehicle performance as closely as possible to the drivers choice. By means of the selection device, the driver is able to adapt the dynamic performance of the vehicle to his or her personal driving style and to different weather and road conditions, thus greatly improving driving safety, particularly in difficult weather and road conditions, such as heavy rainfall, snow or ice.

One example of such a selection device is described in Patent Application WO2004087484A1, in which the selection device comprises a switch built into the steering wheel, and which can be turned to five different settings, each corresponding to a respective dynamic vehicle performance.

Very often, however, drivers tend to miscalculate—in particular, overestimate—their driving skill and, more importantly, their psychophysical condition, with the result that driver-selected dynamic vehicle performance simply reflects the driver's wish, as opposed to the driver's actual psychophysical condition and proficiency, and so amounts to an impairment in driving safety, in the sense of the driver being in control of a vehicle that does not respond adequately to his or her actual psychophysical condition.

The problem of correct psychophysical evaluation of the driver is widely covered in technical literature, which proposes numerous ways of recording psychophysical parameters to evaluate the driver's psychophysical condition, and of employing the evaluation to emit warning signals, to keep the driver alert by acting on internal vehicle systems, and/or to stop the vehicle in the event of the driver losing consciousness. By way of example, the following are just a few of the documents relating to correct psychophysical evaluation of the driver.

Patent Application US2005015016A1 describes a method of determining a driver's mental state and stress by analysing the driver's brain waves.

Patent Application US2003146841A1 describes a method of determining driver stress using various physiological sensors, so appropriate action can be taken if the stress level exceeds a predetermined alarm threshold.

Patent Application GB2394288A describes a steering wheel equipped with sensors for detecting various physical characteristics of the driver, by which to evaluate the driver's psychophysical condition.

Patent Application WO02096694A1 describes monitoring a driver's psychophysical condition, so as to intervene accordingly on various vehicle control units to safeguard the driver. More specifically, in the event of the driver losing consciousness, the vehicle is kept on the right path by acting on the electric power steering control, and is slowed down till it stops, by acting on the cruising control.

U.S. Pat. No. 5,942,979A1 describes monitoring a driver's physical condition. If an emergency situation is detected, the driver is alerted by visual and acoustic signals, and the vehicle can be stopped automatically by acting on the brake and/or injection system.

All the driver psychophysical evaluation solutions described in literature, however, relate to determining and controlling imminent-hazard situations, in which the driver is drowsy or unconscious, and none as yet have investigated the possibility of using physiological parameters to enhance driving pleasure and reduce driving fatigue.

Patent Application WO2007090896A1 describes a method of controlling a driver-operated vehicle, which comprises the steps of: recording a number of psychophysical driver parameters by means of respective biometric and psychometric sensors; evaluating the driver's psychophysical condition as a function of the psychophysical parameters recorded by the biometric and psychometric sensors; and accordingly adjusting the dynamic performance of the vehicle to the driver's psychophysical condition. Evaluating the driver's psychophysical condition as a function of the psychophysical parameters recorded by the biometric sensors, however, is extremely complicated, on account of the difficulty in determining a precise connection between the psychophysical parameters recorded by the biometric and psychometric sensors and the actual psychophysical condition of the driver, and is complicated even further by the wide range of parameter values assumed from one person to another. For example, the threshold value indicating a fast heart rate varies widely from one person to another (typically, the better shape a person is in, the lower the heart rate is at rest).

DISCLOSURE OF THE INVENTION

It is an object of the present invention to provide a vehicle control method designed to eliminate the drawbacks of the above known methods, and which, in particular, provides for enhancing driving pleasure and reducing driving fatigue.

According to the present invention, there is provided a vehicle control method as claimed in the accompanying Claims.

BRIEF DESCRIPTION OF THE DRAWINGS

A non-limiting embodiment of the present invention will be described by way of example with reference to the accompanying drawings, in which.

PREFERRED EMBODIMENTS OF THE INVENTION

Figure 1:
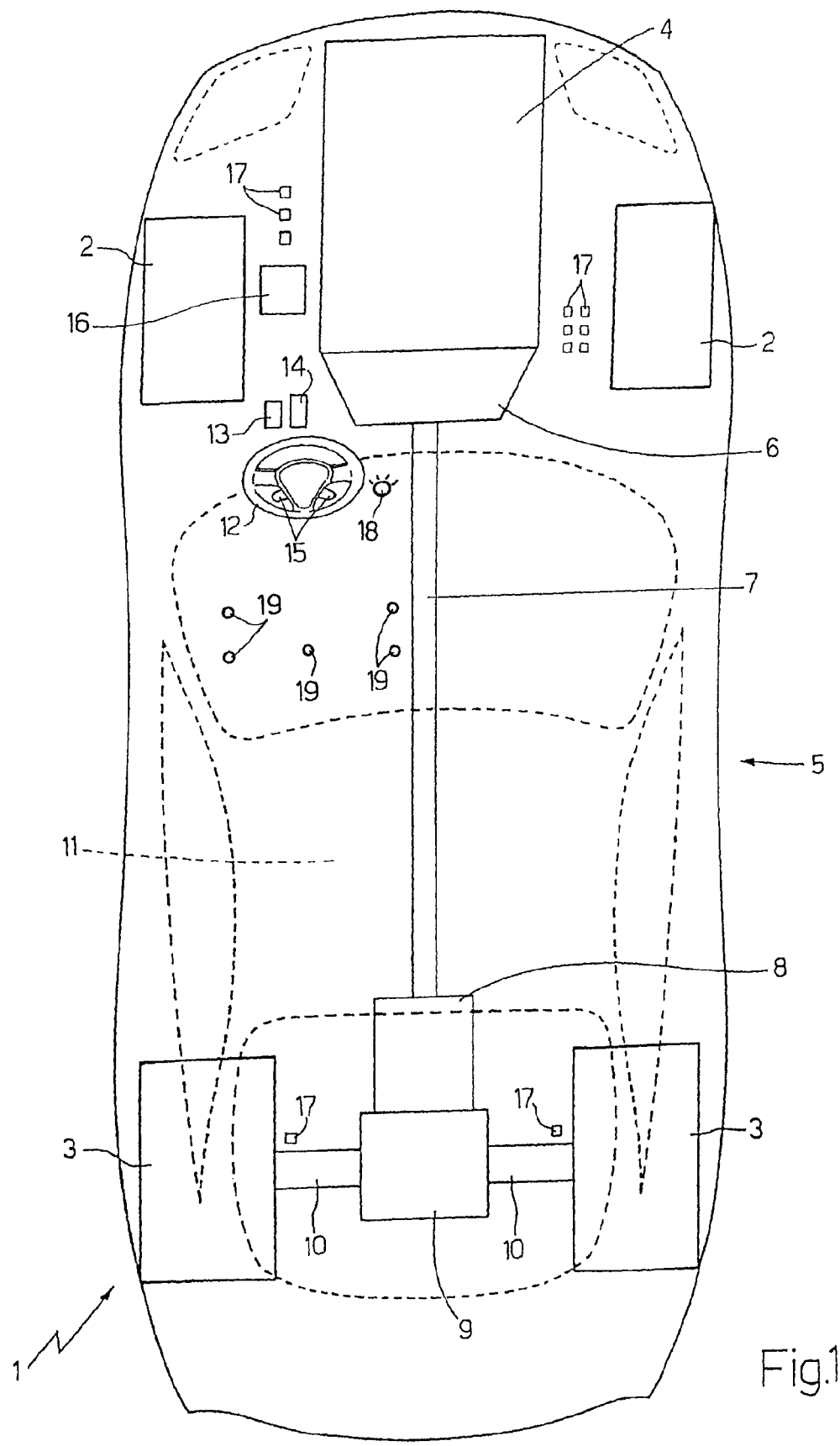
FIG. 1 shows a schematic plan view of a passenger car implementing the control method according to the present invention.

Number 1 in FIG. 1 indicates a passenger car comprising two front wheels 2; two rear drive wheels 3; and a front internal-combustion engine 4 for producing torque which is transmitted to rear drive wheels 3 by a power train 5.

Power train 5 comprises a clutch 6, which is housed in a housing integral with engine 4, and connects the drive shaft of engine 4 to a propeller shaft 7 terminating in a mechanical power transmission 8 at the rear. A self-locking differential 9, with electronic lock percentage control, is cascade connected to transmission 8; and two axle shafts 10 extend from the differential, and are each integral with a respective rear drive wheel 3.

Car 1 also comprises an electronically controllable brake system which acts on wheels 2 and 3; and a known, electronically-controlled-response suspension system (not shown in detail).

Car 1 also comprises an interior 11 housing a steering wheel 12 for imparting a turn angle to front wheels 2; a brake pedal 13 controlling the brake system; an accelerator pedal 14 controlling the torque of engine 4; and a device 15 connected to steering wheel 12 to control transmission 8.

Car 1 comprises an electronic central control unit 16 for controlling operation of the active components of car 1, and which is connected to a number of sensors 17 arranged inside car 1 to real-time record respective dynamic parameters of car 1, such as the travelling speed of car 1, the turn angle of car 1, the yaw speed of car 1, lateral acceleration of car 1, longitudinal acceleration of car 1, the rotation speed of each wheel 2 or 3, and the torque of engine 4. Electronic central control unit 16 may obviously comprise a number of physically separate processing units connected, for example, by a data BUS; and, as opposed to a physical sensor 17, one or more parameters of car 1 may be determined using an estimation algorithm implemented by electronic central control unit 16.

Electronic central control unit 16 performs the functions of various electronic driving-aid devices, and in particular prevents blocking of wheels 2 and 3 when braking (ABS function), prevents skidding of rear drive wheels 3 (ASP function), controls the stability of car 1 (ESP function), and electronically controls suspension response, power-assist of transmission 8, and lock percentage of self-locking differential 9. Electronic central control unit 16 also modifies the operating parameters of the active parts of car 1 (typically, engine 4 and the electronic driving-aid devices referred to above) to modify the dynamic performance of car 1.

Figure 2:
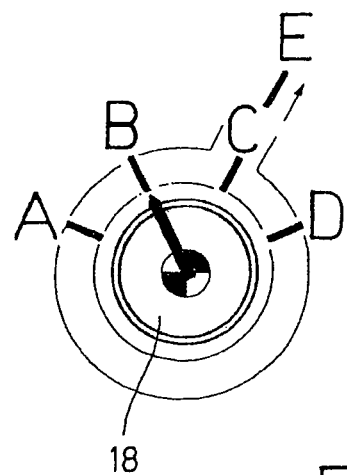
FIG. 2 shows a larger-scale detail of FIG. 1.

To allow the driver to actively select the dynamic performance of car 1, a selection device 18 (shown more clearly in FIG. 2) is provided in interior 11 of car 1, and can be operated by the driver to communicate a chosen dynamic performance of car 1 to electronic central control unit 16. As shown in FIG. 2, selection device 18 can be set to five settings (indicated A-E for simplicity), each corresponding to a respective dynamic performance of car 1.

Interior 11 also houses various (preferably non-invasive) biometric and psychometric sensors 19 for recording and transmitting to electronic central control unit 16 the values of a number of psychophysical parameters of the driver of car 1. The psychophysical parameters recorded by sensors 19 are divided into physical parameters, measured directly on the driver's body, and gestural parameters, measured indirectly by recording the way in which the driver interfaces with the controls of car 1.

By way of example, the physical parameter biometric sensors 19 may comprise a piezoelectric measuring device for measuring the driver's respiration; a device for measuring the driver's blood pressure and heart rate (electrocardiogram); a television camera for monitoring the driver's eyes (blink rate) to determine the driver's alertness; a device for monitoring the electric activity of the driver's brain (electroencephalogram); a device for recording the driver's surface temperature; and a device for recording the conductivity of the driver's skin (i.e. to determine the degree of perspiration).

By way of example, gestural parameter biometric sensors 19 may comprise a device for recording the driver's grip on steering wheel 12; a facial television camera for recording the driver's facial expression and mood (relaxed, happy, sad, worried, anxious, etc.); a television camera for recording the driver's gestures and movements on the seat; and a device for recording the frequency and speed with which the driver operates the controls of car 1.

In actual use, electronic central control unit 16 records the values of a number of psychophysical parameters of the driver over a first measuring interval, and accordingly makes a first psychophysical evaluation of the driver. At the end of the first measuring interval, electronic central control unit 16 records the values of the psychophysical parameters of the driver over a second measuring interval, following the first, and accordingly makes a second psychophysical evaluation of the driver. In one possible embodiment, electronic central control unit 16 may allow a given time lapse between two measuring intervals.

At the end of the second measuring interval, electronic central control unit 16 compares the first and second psychophysical evaluation of the driver to determine the change in the driver's psychophysical condition between the two measuring intervals; at which point, electronic central control unit 16 may, if necessary/possible, alter the dynamic performance of car as a function of the driver's psychophysical condition, to adapt the dynamic performance of car 1 to the change in the driver's psychophysical condition.

Electronic central control unit 16 compares the first and second psychophysical evaluation of the driver to, determine whether the change in the driver's psychophysical condition tends towards satisfaction or dissatisfaction. Accordingly, electronic central control unit 16 increases the response of car 1 to driver control, if the change in the driver's psychophysical condition tends towards satisfaction; reduces the response of car 1 to driver control, if the change in the driver's psychophysical condition tends towards dissatisfaction; and makes no change to the response of car 1 to driver control, if the satisfaction/dissatisfaction change between the two psychophysical evaluations of the driver is insignificant (i.e. below a given threshold value). Whichever the case, electronic central control unit 16 can obviously make no change to the response of car 1 over and above or below certain limits depending on technical, intrinsic safety, and handling restrictions (car 1 can be neither too responsive or too unresponsive to driver control).

Electronic central control unit 16 estimates the driver's satisfaction/dissatisfaction level by analysing the driver's physical parameter values (e.g. heart rate, blood pressure, and skin conductivity).

In one possible embodiment, electronic central control unit 16 also compares the first and second psychophysical evaluation of the driver to determine whether the change in the driver's psychophysical condition tends towards excitement or relaxation. Accordingly, electronic central control unit 16 increases the response of car 1 to driver control, if the change in the driver's psychophysical condition tends towards excitement; reduces the response of car 1 to driver control, if the change in the driver's psychophysical condition tends towards relaxation; and makes no change to the response of car 1 to driver control, if the excitement/relaxation change between the two psychophysical evaluations of the driver is insignificant (i.e. below a given threshold value).

Electronic central control unit 16 estimates the driver's excitement/relaxation level by analysing the driver's gestural parameter values (e.g. how often and how fast the driver operates the controls of car 1).

In a preferred embodiment, electronic central control unit 16 also determines the context in which car 1 is driven (e.g. in city traffic, cruising along main roads or motorways, racing along main roads or motorways, or racing on track), and the driver's psychophysical condition is evaluated as a function of psychophysical parameters and the context in which car 1 is driven. In other words, it has been observed that the context in which car 1 is driven may have a significant influence on the driver's psychophysical condition. For example, a minor stress condition is normal when driving in city traffic, but is not when cruising along main roads or motorways; a stress condition is normal immediately following emergency steps (e.g. sharp braking when cruising along a main road) or in long motorway queues; or a heightened state of alertness is normal when on-track racing, but is not when cruising along main roads or motorways. Knowing the context in which car 1 is driven therefore enables a more accurate, reliable evaluation of the driver's psychophysical condition on the basis of the driver's psychophysical parameter values over the relative measuring interval.

The context in which car 1 is driven is determined as a function of the performance time pattern and/or the location of car 1, which are recorded by electronic central control unit 16. In other words, knowing the location of car 1 (city, main road, motorway, track, etc.) and its performance (slow, fast, competitive driving, queuing, etc.), it is possible to determine the context in which car 1 is driven. For example, sharp braking followed by a prolonged stop is a clear indication of an emergency situation most likely resulting in considerable driver stress.

As stated, the dynamic performance of car 1 is modified by altering the operating parameters of active parts of car 1, e.g. engine 4, the electronic driving-aid devices referred to above, and driver control of the control devices (i.e. steering wheel 12, brake pedal 13, accelerator pedal 14, and device 15 controlling transmission 8).

Figure 3:
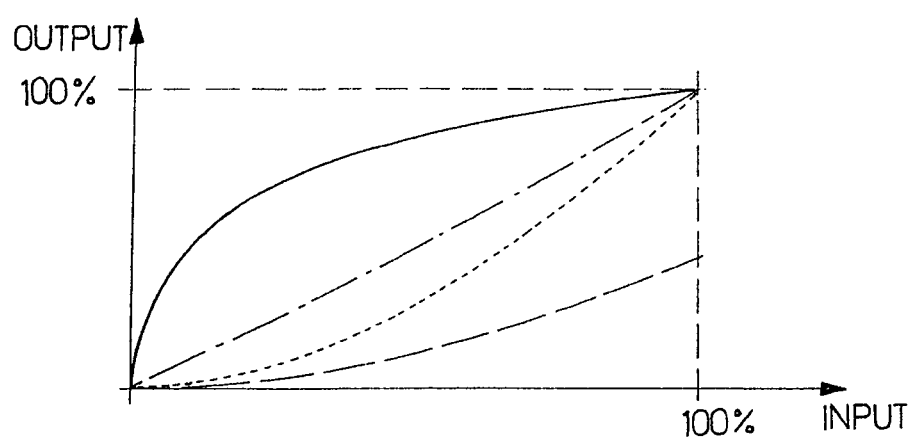
FIG. 3 shows a graph of various transfer functions employed in interpreting driving control of the FIG. 1 car.

The driver controls the car by acting physically on a number of control devices (steering wheel 12, brake pedal 13, accelerator pedal 14, and device 15 controlling transmission 8), the positions of which are recorded by respective sensors (not shown) and transmitted to electronic central control unit 16, which interprets the positions by means of corresponding transfer functions. Adjusting the response of car 1 to driver control comprises adjusting the gain of the transfer functions. An example of this is shown in FIG. 3, which shows four schematic transfer functions which assign a given physical position of a control device (INPUT) a corresponding drive (OUTPUT). The steeper the transfer function is (i.e. the higher the gain of the transfer function), the more direct and faster the response to a driving command is.

In a preferred embodiment, increasing the response of car 1 to driver control comprises delaying and/or reducing intervention of various electronic driving-aid devices; and, conversely, reducing the response of car 1 to driver control comprises accelerating and/or increasing intervention of various electronic driving-aid devices.

The method described provides for making a differential, as opposed to absolute, evaluation of the driver's psychophysical condition, i.e. compares two successive psychophysical evaluations of the driver to determine the change in the driver's psychophysical condition, and does not need to determine the driver's absolute psychophysical condition. In other words, the method described does not need to determine whether the driver is satisfied/dissatisfied or relaxed/excited (which is extremely difficult to do judge, in that, given the same psychophysical parameter recordings by the sensors, the driver's actual psychophysical condition may vary considerably from one person to another), but simply determines whether the driver becomes more satisfied or less dissatisfied, or more excited or more relaxed.

By way of example, regardless of a person's heart rate at rest (which may vary considerably from one person to another), an increase in heart rate is always an indication of greater stress of the autonomic nervous system. Therefore, differentially evaluating the driver's psychophysical parameters is much more accurate and reliable than an absolute evaluation.

By making a differential, as opposed to absolute, psychophysical evaluation of the driver, the method described is much more precise and reliable in adapting dynamic performance of car 1 accordingly.

Electronic central control unit 16 is therefore able to modify the dynamic performance of car 1 to adapt it to the driver's psychophysical condition, i.e. is able to adapt the dynamic performance of car 1 automatically as a function of the driver's psychophysical condition, and independently of the driver's conscious preference. It is important to note that the dynamic performance of car 1 may be modified to enhance driving safety in the case of a tired or unresponsive driver, and also to enhance driving pleasure and/or performance in the case of an alert, responsive driver.

The invention claimed is:

1. A method of controlling a driver-operated vehicle, in which the driver controls the vehicle by acting physically on a number of control devices, the positions of which are recorded by respective sensors and transmitted to an electronic central control unit, which interprets the positions by means of corresponding transfer functions; the method comprising the steps of:

recording the values of a number of psychophysical parameters of the driver over a first measuring interval;

making a first evaluation of the driver's psychophysical condition on the basis of the driver's psychophysical parameter values over the first measuring interval;

recording the values of the driver's psychophysical parameters over a second measuring interval following the first measuring interval;

making a second evaluation of the driver's psychophysical condition on the basis of the driver's psychophysical parameter values over the second measuring interval;

comparing the first and second evaluation of the driver's psychophysical condition to determine a change in the driver's psychophysical condition; and modifying the dynamic performance of the vehicle as a function of the driver's psychophysical condition, to adapt dynamic performance of the vehicle to the change in the driver's psychophysical condition;

the method is characterized in that it comprises the further steps of:

comparing the first and second evaluation of the driver's psychophysical condition to determine whether the change in the driver's psychophysical condition tends towards satisfaction or dissatisfaction and towards excitement or relaxation;

increasing response of the vehicle to driver control, if the change in the driver's psychophysical condition tends towards satisfaction or tends towards excitement, by adjusting the gain of the transfer functions to have a more direct and faster response to driving commands;

reducing response of the vehicle to driver control, if the change in the driver's psychophysical condition tends towards dissatisfaction or towards relaxation, by adjusting the gain of the transfer functions to have a less direct and slower response to driving commands;

making no change in response of the vehicle to driver control, if the satisfaction/dissatisfaction or excitement/relaxation change between the two evaluations of the driver's psychophysical condition is insignificant;

evaluating the driver's satisfaction/dissatisfaction level by analysing the values of physical parameters of the driver; and evaluating the driver's excitement/relaxation level by analysing the values of gestural parameters of the driver.

2. A method as claimed in claim 1, and comprising the further step of allowing a time lapse between the end of the first measuring interval and the start of the second measuring interval.

3. A method as claimed in claim 1, wherein the physical parameters of the driver used to evaluate the satisfaction/dissatisfaction level comprise heart rate, blood pressure, and skin conductivity.

4. A method as claimed in claim 1, wherein the gestural parameters of the driver used to evaluate the excitement/relaxation level comprise how often the controls of the vehicle are operated, and how fast the controls of the vehicle are operated.

5. A method as claimed in claim 1, and comprising the further steps of:
   determining the context in which the vehicle is driven;
   making an evaluation of the driver's psychophysical condition on the basis of the driver's psychophysical parameter values over the relative measuring interval, and as a function of the context in which the vehicle (1) is driven over the relative measuring interval.

6. A method as claimed in claim 5, and comprising the further steps of:
   recording the performance time pattern of the vehicle and/or the location of the vehicle (1);
   determining the context in which the vehicle is driven as a function of the performance time pattern of the vehicle and/or of the location of the vehicle.

7. A method as claimed in claim 1, wherein increasing response of the vehicle to driver control comprises delaying and/or reducing intervention of various electronic driving-aid devices; and, conversely, reducing response of the vehicle to driver control comprises accelerating and/or increasing intervention of various electronic driving-aid devices.

* * * * *